United States Patent
Li et al.

(10) Patent No.: US 9,603,950 B1
(45) Date of Patent: Mar. 28, 2017

(54) COMPOUNDS OF IMAGING AGENT WITH HDAC INHIBITOR FOR TREATMENT OF ALZHEIMER SYNDROME AND METHOD OF SYNTHESIS THEREOF

(71) Applicants: Ming-Hsin Li, Taoyuan (TW); Chyng-Yann Shiue, Taoyuan (TW); Han-Chih Chang, Taoyuan (TW); Han-Hsiang Chu, Taoyuan (TW)

(72) Inventors: Ming-Hsin Li, Taoyuan (TW); Chyng-Yann Shiue, Taoyuan (TW); Han-Chih Chang, Taoyuan (TW); Han-Hsiang Chu, Taoyuan (TW)

(73) Assignee: INSTITUTE OF NUCLEAR ENERGY RESEARCH, Longtan, Taoyuan (TW)

( * ) Notice: Subject to any disclaimer, the term of this patent is extended or adjusted under 35 U.S.C. 154(b) by 0 days.

(21) Appl. No.: 14/922,159

(22) Filed: Oct. 25, 2015

(51) Int. Cl.
*C07C 237/40* (2006.01)
*C07C 231/12* (2006.01)
*A61K 51/04* (2006.01)
*C07C 233/80* (2006.01)

(52) U.S. Cl.
CPC .......... *A61K 51/04* (2013.01); *C07C 231/12* (2013.01); *C07C 233/80* (2013.01); *C07C 237/40* (2013.01)

(58) Field of Classification Search
CPC ...... A61K 50/04; A61K 51/04; C07C 237/40; C07C 233/80; C07C 231/12
See application file for complete search history.

(56) References Cited

U.S. PATENT DOCUMENTS

| 7,868,205 B2 * | 1/2011 | Moradei | C07C 233/25 544/295 |
| 9,108,943 B2 * | 8/2015 | Petukhov | C07C 247/16 |
| 2010/0249123 A1 * | 9/2010 | Bonnet | C07C 235/56 514/230.5 |

OTHER PUBLICATIONS

Bressi et al, Bioorganic & Medicinal Chemistry Letters, 2010, 20(10), 3142-3145.*

* cited by examiner

*Primary Examiner* — Shailendra Kumar

(57) ABSTRACT

A method of synthesizing a compound of imaging agent with HDAC (histone deacetylase) inhibitor consists of two parts, the first part of the method is to provide the inhibitor of HDAC with a compound of imaging agent that includes HDAC inhibitor BNL-26 ($C_{22}H_{23}N_3O$) and its analogs to be labeled with radionuclide F-18, producing a series of new nuclear medicine tracers: BNL-26-$CH_2CH_2$18F, BNL-26a-$CH_2CH_2$18FF, BNL-26b-$CH_2CH_2$18F, BNL-26c-$CH_2CH_2$18F and BNL-26d-$CH_2CH_2$18F. These nuclear medicine with imaging agents can be used as a tracer in vivo binding to over-expression HDAC and produce a HDAC nuclear medicine imaging effect to serve for clinical diagnosis. The second part of the method is to provide a slightly adjusted a structural framework of BNL-26 and use pyridine to substitute the benzene ring of the BNL-26 structure, and then synthesize with other substituent to produce a series of additional 30 more HDAC inhibitors, named from Iner-1 to Iner-30 compounds.

3 Claims, No Drawings

COMPOUNDS OF IMAGING AGENT WITH HDAC INHIBITOR FOR TREATMENT OF ALZHEIMER SYNDROME AND METHOD OF SYNTHESIS THEREOF

BACKGROUND OF THE INVENTION

1. Field of the Invention

The present invention relates to a compound synthesis method for nuclear medicine imaging agent for HDAC (histone deacetylase) inhibitor, in particular, to compounds of imaging agent that includes HDAC inhibitor BNL-26 ($C_{22}H_{23}N_3O$) and a plurality of its analogue compounds to be labeled with radionuclide F-18, and to use of pyridine to substitute the benzene ring of the BNL-26 structure and synthesizing with other substituent to produce a series of novel HDAC inhibitors for diagnosing cancer and Alzheimer's disease.

2. Description of the Related Art

Histone deacetylase inhibitors (HDAC inhibitors or HDACi) are medication for controlling histone deacetylase in the human body and being used to treat cancer and neurodegeneration disease by the medical research in medical industries. These specific mechanisms of inhibitor are disclosed in the characterization of genomics approaches presented in the literature, for example, Richon et al. found that HDAC inhibitors may be used to regulate the tumor suppression function of P53 through introducing cyclin-dependent kinase inhibitor P21(WAF1).

Conventional studies about cancer and development dysplasia of organs like colon, rectum, cervix, stomach, and prostate have not been a satisfactory outcome. Besides, the research of natural aging indicates that cerebral atrophy is an early sign of neurodegeneration related to cognitive deficit and loss of memory, and dementia like Alzheimer's disease usually leads the patient of such disease to an unrecoverable situation for unknown causes and lacking of a measure of early diagnosis of Alzheimer's disease. And early discovery, diagnosis, and curing of cancer and Alzheimer's disease depend on diagnostic methods is still in vain. In the prior art, U.S. Pat. No. 7,868,205, it disclosed that o-amino benzamide HDAC inhibitors had a much bigger but flat aromatic and heteroaromatic substituents such as phenyl, furyl, thienyl and the like para to the amino moiety. Also, U.S. Pat. No. 9,108,943 disclosed studies of a series of photoreactive potent and selective HDACs 1 and 2 benzamide based probes.

According to research in cancer and development dysplasia of body organs, over-expression of histone deacetylase 2 (HDAC-2) does exist in both cases and in many cases of those diseases, such as colon, rectum, cervix, stomach, and prostate etc. Furthermore, the research in recent years also pointed out that chromatin modification in the brain cells is related to the memory formation which is influenced intensely by histone deacetylase, for example, a mouse with abnormal secretion of histone deacetylase enzyme could lose part of memory as same as the symptom of Alzheimer's disease. Thus, dosing histone deacetylase inhibitors will be a new hope to the treatment of cancer and Alzheimer's disease.

HDAC inhibitors have been a hot spot of medication research as a targeted anti-tumor medication. The existing HDAC inhibitors are mainly divided into four categories according to structure, comprising: (a) hydroxamic acids, suchlike Vorinostat; (b) cyclic tetrapeptide, suchlike Romidepsin (FK228) and depsipeptide; (c) benzoylamide, suchlike MS-275 and SC-027; (d) short-chain fatty acid, suchlike valproic acid and butyrate. The efficacies of HDAC inhibitors for treating hematologic malignancies and solid tumors are confirmed both in vivo and vitro experiments. The vitro experiment confirmed that HDAC inhibitors exhibits good anti-tumor effect to the tumor cell of bladder, bone, breast, uterus, central nervous system, esophagus, lung, ovary, pancreas, or prostate by tumor cell apoptosis, proliferation inhibition and cell cycle arrest, and many types of HDAC inhibitors are entering phase I or II or III of clinical study for their multiple paths and high efficiencies for anticancer.

Vorinostat (suberoylanilide hydroxamic acid, SAHA) and Romidepsin (cyclic peptide) are approved by FDA to be listed for applying to cutaneous T-cell lymphoma (CTCL) and the application of the treatment of solid tumor is also in clinical trials. The benzoylamide HDAC inhibitors chidamide developed by Chipscreen Ltd. is approved by FDA for clinical research in USA to confirm that the new type HDAC inhibitors in small doses and low concentration can induce tumor cell differentiation and selective apoptosis for anti tumor proliferation and be non-toxic to normal cells.

By analysis of tumor diagnoses in identification of whether a tumor exists, the nature of tumors, benign or malignant ones, phase of tumor stage and metastasis are all very important, it revealed that most tumors are often found lately, and at the time it has already caused damage to one or more functions of vital organs, and even has been transferred to the entire body. Therefore, the key question is how to treat tumor in early detections, but detection of tumors in earlier stage is still very difficulty.

Diagnosis of Alzheimer's disease (referred to as AD) includes basic check neuropsychological tests, blood routine, biochemical test of liver and kidney functions, vitamin B12 level, thyroid function, syphilis serology, and brain computed tomography or magnetic resonance angiography. High order PET positron imaging diagnostic methods exploiting amyloid hypothesis as the theoretical basis for drugs include F-18-AV45 and F-18-PIB two kinds, whereas the microtubule associated protein hypothesis (Tau hypothesis) as the theoretical basis for drug is not yet available.

Clinical diagnosis with imaging inspection includes X-ray examination, ultrasonography, magnetic resonance imaging, X-ray tomography (abbreviated CT) and radioisotope examination. Early diagnosis of tumor and Alzheimer's disease has a role of important significance, because only a early diagnosis and treatment can get better result of treatment. However, due to various objective and subjective reasons, the majority of patients in the treatment or diagnosis of tumors that already advanced in midterm or later, and the treatment effect is not satisfactory in this case. Although the diagnosis method of tumor is developing rapidly, but many tumor screening methods are not effective enough, and it takes that tumors need to be of 1~1.5 cm in diameter size before it can be clearly displayed in an imaging inspection.

A general blood test accuracy is insufficient, for example, a prostate-specific antigen (PSA) is a glycoprotein. This antigen can only be produced by prostate cells, when a prostate disease occurs, such as prostate tumor, a prostate hyperplasia cell will produce an excess of PSA that leads to the PSA level in the blood increases. Doctors may analyze blood PSA levels to determine the possibility of patients suffering from a prostate tumor. There are various factors leading to elevated PSA, such as prostate infection and benign prostate hyperplasia. Moreover, not all prostate cancer patients exhibited elevated PSA, thus a PSA test result can not be confirmed for a candidate of prostate cancer patient. Diagnosis of Alzheimer's disease with the latest PET drugs F-18-AV45 and F-18-PIB, the imaging of PET can only be diagnosed whether an Alzheimer's disease exists, however, human aging phenomenon also reveals an identical reaction with the same image, and thus it is difficult to confirm that a patient is suffering from Alzheimer's disease with the image presented.

SUMMARY OF THE INVENTION

It revealed in a previous study of the present invention that the use of BNL-26 inhibitor labeled with 11C not only exhibited a good inhibitory effect of HDAC1 and HDAC2, while its ability to penetrate the brain blood vessel barrier is also very good.

The primary object of the present invention is to provide a method of synthesizing compounds of imaging agent with HDAC inhibitor including two main parts, the first part of the method is to provide the inhibitor of histone deacetylase (HDAC) with a compound of imaging agent that includes HDAC inhibitor BNL-26 ($C_{22}H_{23}N_3O$) and its analogues to be labeled with a radionuclide F-18, producing a series of new nuclear medicine tracers: BNL-26-CH$_2$CH$_2$18F, BNL-26a-CH$_2$CH$_2$18FF, BNL-26b-CH$_2$CH$_2$18F, BNL-26c-CH$_2$CH$_2$18F and BNL-26d-CH$_2$CH$_2$18F. These nuclear medicine with imaging agents of the present invention can be used as a tracer in vivo binding to over-expression HDAC and produce a HDAC nuclear medicine imaging effect to serve for clinical diagnosis.

Another object of the present invention is to provide a slightly adjusted structural framework of BNL-26 and use pyridine to substitute the benzene ring of the BNL-26 structure, and then synthesize with other substituent to produce a series of additional 30 more HDAC inhibitors, named from Iner-1 to Iner-30 compounds. And these compounds can be labeled with a radionuclide F-18 as that of HDAC inhibitor BNL-26.

The two main parts of the compound of the present invention for diagnosis of Alzheimer's development can be used for monitoring an earlier hyperactivity performance of HDAC concentration for neuronal cell injury than a traditional beta amyloid imaging agent, and at the same time be adopted as assessment of therapeutic efficacy. The prior art is capable for diagnosing only at late stage for Alzheimer syndrome, and there is a phenomenon of false positive result.

Therefore, the method of synthesizing a compound of imaging agent with HDAC inhibitor for treatment of Alzheimer syndrome of the present invention shows a high degree of novelty and inventive steps, as will be described in detail.

In the first part of the present invention, it is to provide the inhibitor of HDAC with a compound of imaging agent that includes HDAC inhibitor BNL-26 ($C_{22}H_{23}N_3O$) and its analogues that are to be labeled with a radionuclide F-18, producing a series of new nuclear medicine tracers: BNL-26-CH$_2$CH$_2$18F, BNL-26a-CH$_2$CH$_2$18FF, BNL-26b-CH$_2$CH$_2$18F, BNL-26c-CH$_2$CH$_2$18F, and BNL-26d-CH$_2$CH$_2$18F. These compounds with imaging agents of the present invention can be used as a tracer in vivo binding to over-expression HDAC for clinical diagnosis.

The structure frame of the HDAC inhibitor BNL-26 and its analogues is shown below.

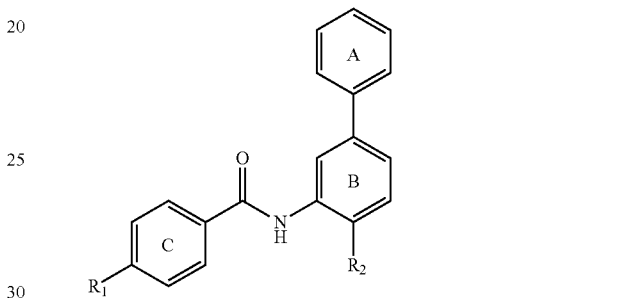

wherein R$_1$ substituent includes —CH$_2$N(CH$_3$)$_2$, —N(CH$_3$)$_2$, —CH(CH$_3$)$_2$, —CH$_2$CH(CH$_3$)$_2$, —CH$_2$CH$_2$CH$_3$; wherein R$_2$ substituent includes —NH$_2$, —COOH.

All synthesized compounds structure of the present invention are shown in the table 1 below.

TABLE 1

| CODE | IUPAC | STRUCTURE |
|---|---|---|
| BNL-26 | N-(4-amino-[1,1'-biphenyl]-3-yl)-4-((dimethylamino)methyl)benzamide | 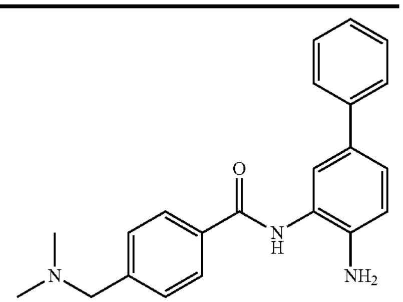 |
| BNL-26a | N-(4-amino-[1,1'-biphenyl]-3-yl)-4-(dimethylamino)benzamide | 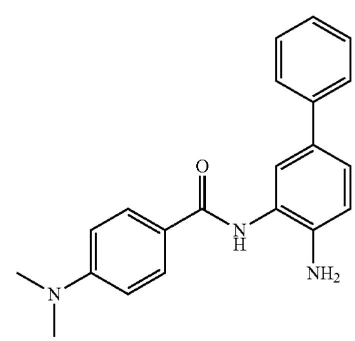 |

TABLE 1-continued

| CODE | IUPAC | STRUCTURE |
|---|---|---|
| BNL-26b | N-(4-amino-[1,1'-biphenyl]-3-yl)-4-isopropylbenzamide | 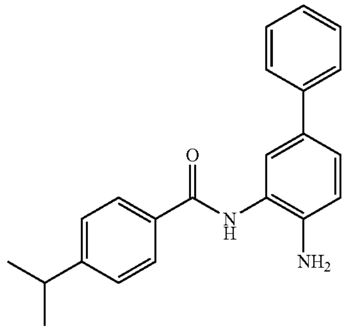 |
| BNL-26c | N-(4-amino-[1,1'-biphenyl]-3-yl)-4-isobutylbenzamide | 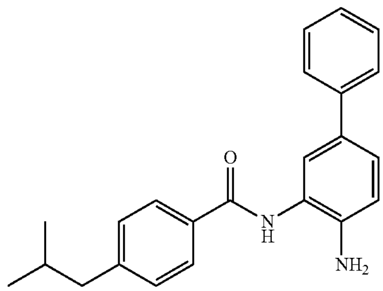 |
| BNL-26d | N-(4-amino-[1,1'-biphenyl]-3-yl)-4-propylbenzamide | 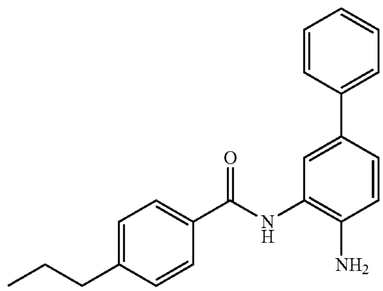 [SMILES: CCCc1ccc(C(=O)Nc2cc(-c3ccccc3)ccc2N)cc1] |

The products listed in the Table 1 above are labeled with F-18 at different locations through various synthesis steps, and each synthesis step is described in the following paragraph, respectively.

1) labeling on the $NH_2$ of the B ring with a F-18 carbon chain structure, such as BNL-26-$(CH_2)n18F$, wherein n=2 or 3, the following reaction steps are represented with n=2. The other four analogues of BNL-26 may also sign on each F-18. Experimental procedures with different sequence can be categorized into two types:

(1) First Type Labeling of BNL-26-$CH_2CH_2{}^{18}F$

Firstly, place di-p-toluene sulfonic acid terephthalate TsOCH2CH2OTs and $^{18}[F]F^-K^+$ APE 2.2.2 in methanol and heating to about 85° C. for about 5 minutes to form TsOCH2CH218F:

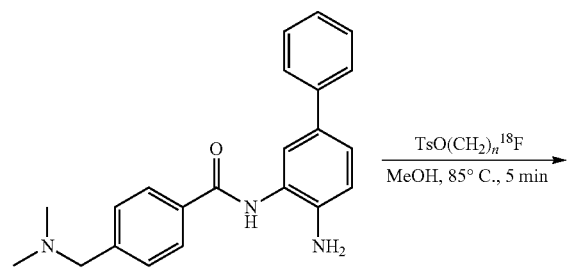

And followed by placing BNL-26 and labeled TsOCH$_2$CH$_2{}^{18}$F in methanol and heating to about 85° C. for about 5 minutes, forming BNL-26-CH$_2$CH$_2{}^{18}$F.

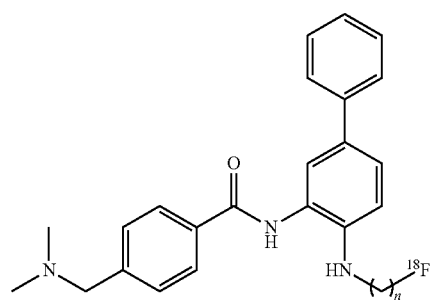

(2) Second Labeling Type of BNL-26-CH$_2$CH$_2$$^{18}$F
Firstly, place TsOCH2CH2OTs and BNL-26 in methanol and heating to about 85° C. for about 5 minutes to form BNL-26-CH$_2$CH$_2$OTs.
And followed by placing BNL-26-CH$_2$CH$_2$OTs and $^{18}$[F] F–K$^+$ APE 2.2.2 in methanol and heating to about 85° C. for about 5 minutes, forming BNL-26-CH$_2$CH$_2$$^{18}$F.
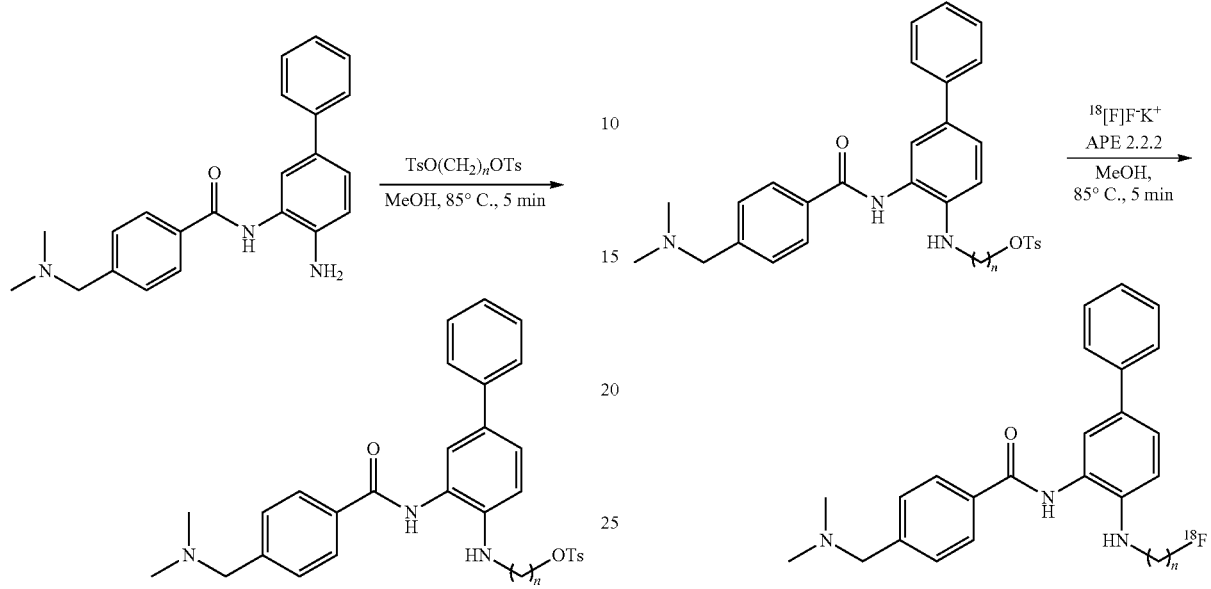
2) Labeling F-18 on the Para-Position of a Benzene Ring:

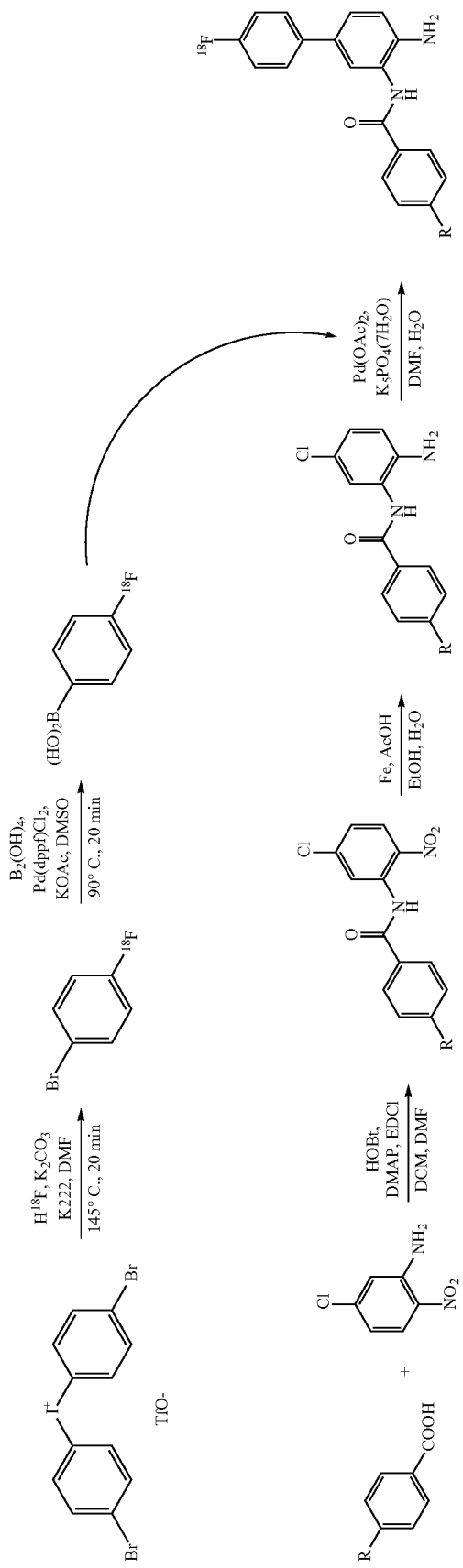

3) Label F-18 on NH2 on the Benzene Ring Through Benzene Amide Structure:

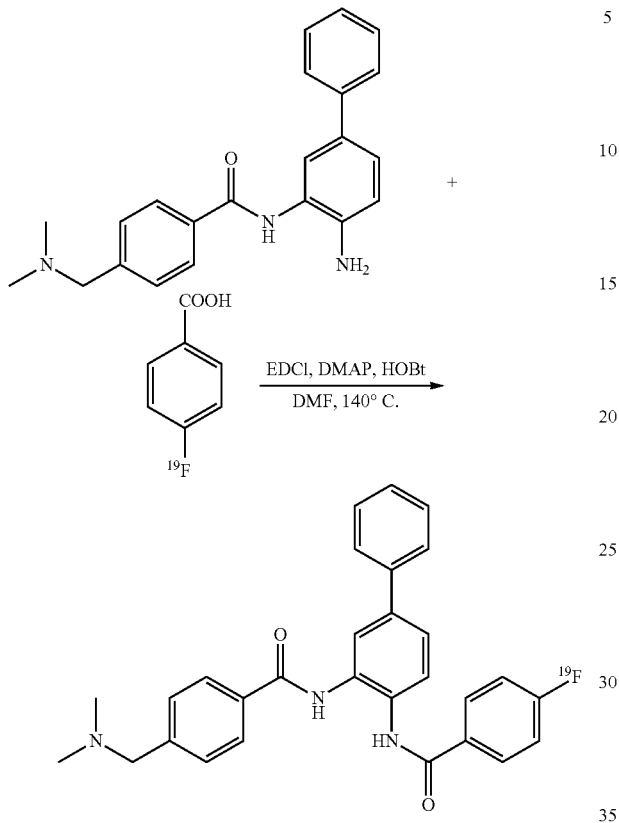

Further, when using RP-C-18 HPLC for separation of the product labeled with 18F, in order to reduce the amount of radiation exposure, a non-radiation F-19 is used as a control standard during separation to effectively reduce the operation time of HPLC.

The present invention intended to provide a novel cancer reactive compounds for diagnosing tumor and Alzheimer's disease by using fluorine-18 or zirconium-89 isotopes positron decay characteristics, resulting in positrons released by its decay, leading to electronic annihilation reactions to take place while encountering cell electrons, generating a pair of 511 keV Gama rays in the opposite direction, and images were obtained through positron radiation tomography (PET).

Whether tumors and Alzheimer disease can be detected at earlier time for timely diagnosis and treatment, it is depending on the diagnostic method to be used. The latest advanced molecular biology for cancer detection, diagnosis and treatment has opened up several new avenues. Although these new pathways are still under study, but very promising. With these newly developed detection methods, it can find subtle changes in cells that can reveal cancer signs earlier. Such new technology also helps to develop treatment programs, since these programs are based on individual differences in the treatment of patients and developed towards the scientific objectives of individual treatment.

The structural framework of the BNL-26 can be slightly adjusted, such as the use of pyridine to substitute benzene ring structure of BNL-26, and using various kinds of substituent on a synthesis base, producing another series of HDAC inhibitors, such as Iner-1, Iner-2, to Iner-30 and so on 30 more additional compounds. The synthesis process is shown below:

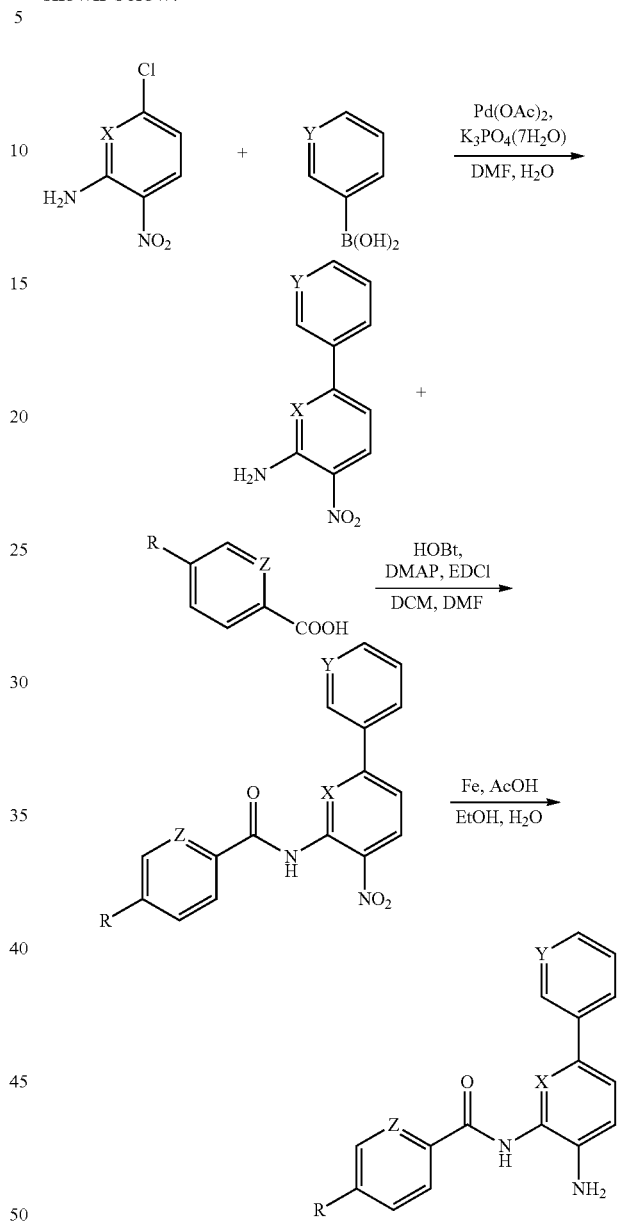

wherein there are three types of substitution: a. X=C; Y=C; Z=N; b. X=C; Y=N; Z=C; c. X=N; Y=C; Z=C; wherein R includes —$CH_2N(CH_3)_2$, —$N(CH_3)_2$, —$CH(CH_3)_2$, —$CH_2CH(CH_3)_2$, —$CH_2CH_2CH_3$.

DETAILED DESCRIPTION OF THE PREFERRED EMBODIMENT

A method of synthesizing compounds of imaging agent with HDAC inhibitor including two main parts:

The first part is to label F18 on different locations through various linkers. There are three types of labeling on different locations. In addition, the products with labeled F-18 also categorised in to types, which are described as follows:

1) Labeling F-18 on the Para-Position of a Benzene Ring:
TABLE 2
| CODE | IUPAC | LogP/PSA | STRUCTURE |
|---|---|---|---|
| BNL-26-F18 | [$^{18}$F]N-(4-amino-4'-fluoro-[1,1'-biphenyl]-3-yl)-4-((dimethylamino)methyl)-benzamide | 3.81/58.36 | 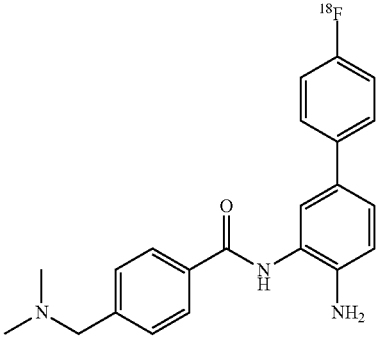 [SMILES: CN(C)Cc1ccc(C(=O)Nc2cc(-c3ccc([18F])cc3)ccc2N)cc1] |
| BNL-26a-F18 | [$^{18}$F]N-(4-amino-4'-fluoro-[1,1'-biphenyl]-3-yl)-4-(dimethylamino)benzamide | 4.15/58.36 | 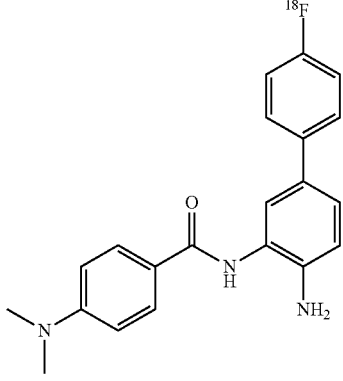 [SMILES: CN(C)c1ccc(C(=O)Nc2cc(-c3ccc([18F])cc3)ccc2N)cc1] |
| BNL-26b-F18 | [$^{18}$F]N-(4-amino-4'-fluoro-[1,1'-biphenyl]-3-yl)-4-isopropylbenzamide | 5.10/55.12 | 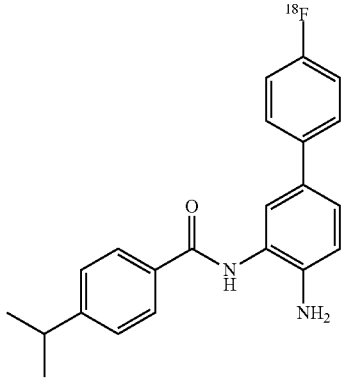 [SMILES: CC(C)c1ccc(C(=O)Nc2cc(-c3ccc([18F])cc3)ccc2N)cc1] |

TABLE 2-continued

| CODE | IUPAC | LogP/PSA | STRUCTURE |
|---|---|---|---|
| BNL-26c-F18 | [¹⁸F]N-(4-amino-4'-fluoro-[1,1'-biphenyl]-3-yl)-4-isobutylbenzamide | 5.52/55.12 | 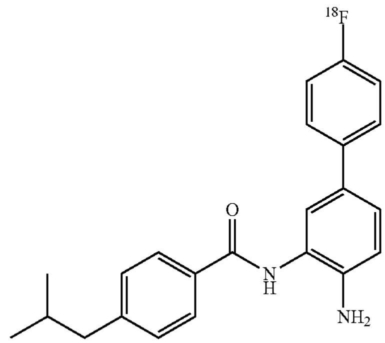 [SMILES: CC(C)Cc1ccc(C(=O)Nc2cc(-c3ccc([18F])cc3)ccc2N)cc1] |
| BNL-26d-F18 | [¹⁸F]N-(4-amino-4'-fluoro-[1,1'-biphenyl]-3-yl)-4-propylbenzamide | 5.19/55.12 | 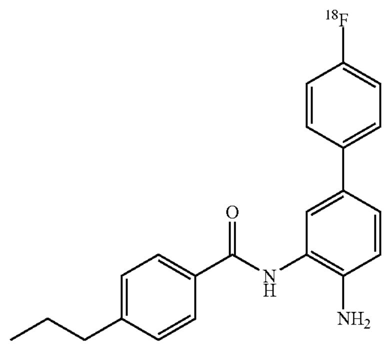 [SMILES: CCCc1ccc(C(=O)Nc2cc(-c3ccc([18F])cc3)ccc2N)cc1] |

2) Labeling F-18 on $NH_2$ of B Benzene Ring:

TABLE 3

| CODE | IUPAC | LogP/PSA | STRUCTURE |
|---|---|---|---|
| BNL-26-CCF18 | [¹⁸F]4-((dimethylamino)methyl)-N-(4-((2-fluoroethyl)amino)-[1,1'-biphenyl]-3-yl)-benzamide | 4.14/44.37 | 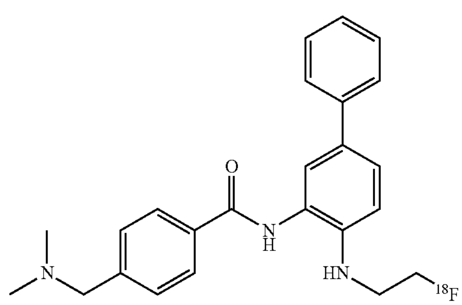 [SMILES: CN(C)Cc1ccc(C(=O)Nc2cc(-c3ccccc3)ccc2NCC[18F])cc1] |
| BNL-26a-CCF18 | [¹⁸F]4-(dimethylamino)-N-(4-((2-fluoroethyl)amino)-[1,1'-biphenyl]-3-yl)-benzamide | 4.19/44.37 | 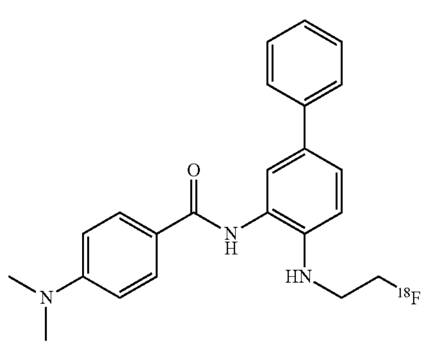 [SMILES: CN(C)c1ccc(C(=O)Nc2cc(-c3ccccc3)ccc2NCC[18F])cc1] |

TABLE 3-continued

| CODE | IUPAC | LogP/PSA | STRUCTURE |
|---|---|---|---|
| BNL-26b-CCF18 | [$^{18}$F]N-(4-((2-fluoroethyl)-amino)-[1,1'-biphenyl]-3-yl)-4-isopropylbenzamide | 5.44/41.13 | 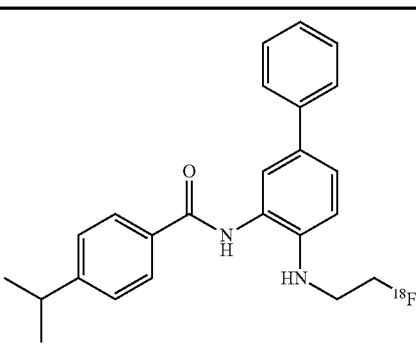 |
| BNL-26c-CCF18 | [$^{18}$F]N-(4-((2-fluoroethyl)-amino)-[1,1'-biphenyl]-3-yl)-4-isobutylbenzamide | 5.85/41.13 | 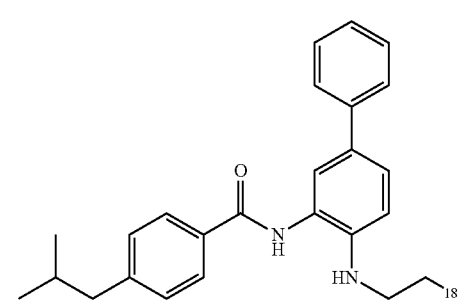 |

3) Label F-18 on NH2 of the Benzene Ring B Through Benzene Amide Structure:

TABLE 4

| CODE | IUPAC | LogP/PSA | STRUCTURE |
|---|---|---|---|
| BNL-26-CBF18 | [$^{18}$F]4-((dimethylamino)methyl)-N-(4-(4-fluorobenzamido)-[1,1'-biphenyl]-3-yl)benzamide | 5.42/61.44 | 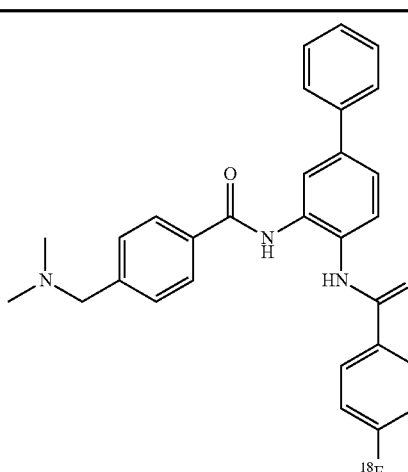 |

The second part of the method is to provide a slightly adjusted structural framework and use pyridine to substitute the benzene ring of the BNL-26 structure, and then synthesize with other substituent to produce a new type of compound of HDAC inhibitor with imaging agent. The substitution of benzene ring A, B and C with pyridine is shown below.

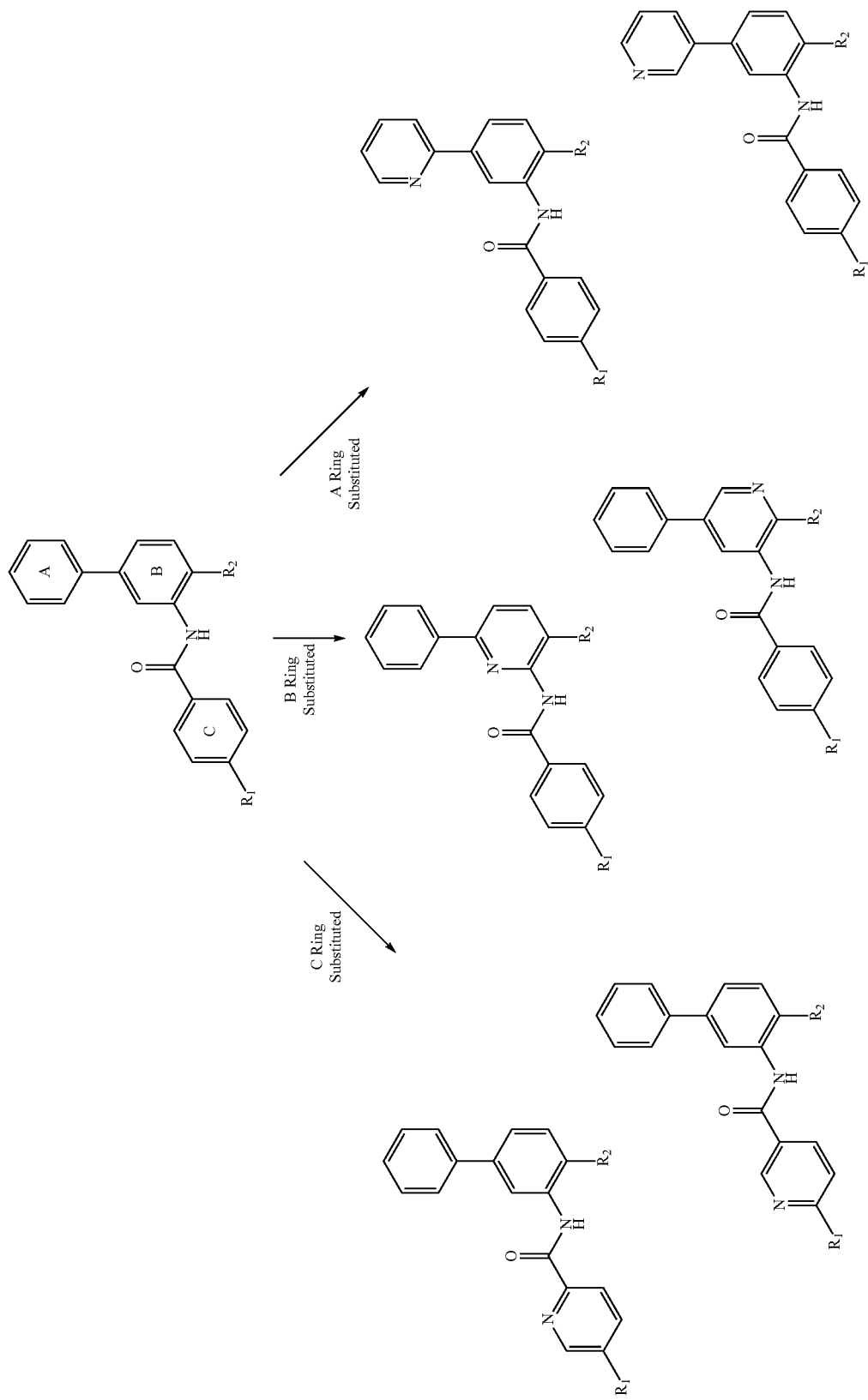

wherein the synthesis substituent R1 includes —CH$_2$N(CH$_3$)$_2$, —N(CH$_3$)$_2$, —CH(CH$_3$)$_2$, —CH$_2$CH(CH$_3$)$_2$, —CH$_2$CH$_2$CH$_3$; wherein the synthesis substituent R2 includes —NH$_2$, a detailed description as follows:

1) Benzene Ring a Substituted with Pyridine:

TABLE 5

| CODE/<br>LogP/PSA | STRUCTURE |
|---|---|
| Iner-1/2.74/70.72 | 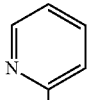 |
| Iner-2/3.08/70.72 | 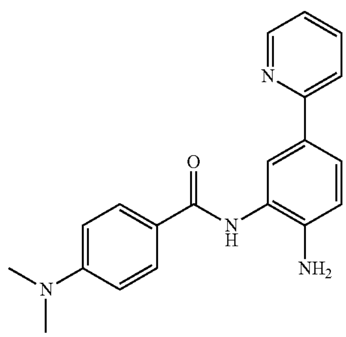 [SMILES: CN(C)c1ccc(C(=O)Nc2cc(-c3ccccn3)ccc2N)cc1] |
| Iner-3/4.03/67.48 | 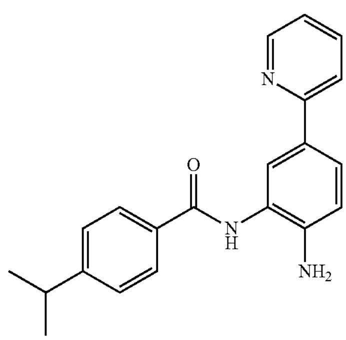 [SMILES: CC(C)c1ccc(C(=O)Nc2cc(-c3ccccn3)ccc2N)cc1] |
| Iner-4/4.45/67.48 | 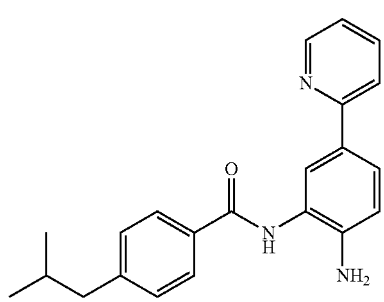 [SMILES: CC(C)Cc1ccc(C(=O)Nc2cc(-c3ccccn3)ccc2N)cc1] |

TABLE 5-continued

| CODE/<br>LogP/PSA | STRUCTURE |
|---|---|
| Iner-5/4.12/67.48 | 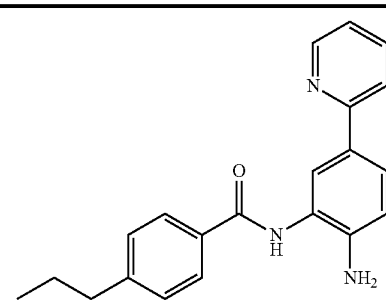 |
| Iner-6/2.32/70.72 | 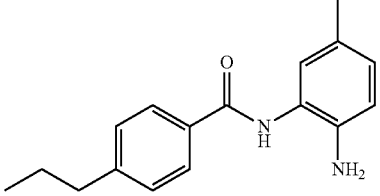 |
| Iner-7/2.66/70.72 | 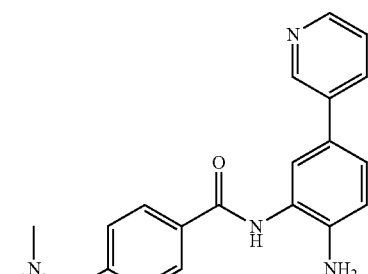 |
| Iner-8/3.61/67.48 | 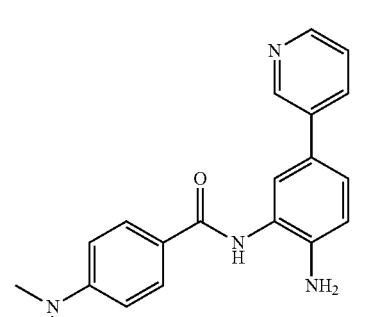 |
| Iner-9/4.03/67.48 | 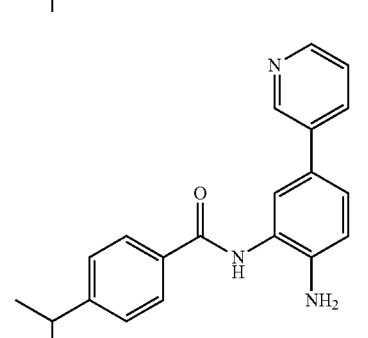 |

TABLE 5-continued

| CODE/LogP/PSA | STRUCTURE |
|---|---|
| Iner-10/3.7/67.48 | (structure) |

2) Benzene Ring B Substituted with Pyridine:

TABLE 6

| CODE/LogP/PSA | STRUCTURE |
|---|---|
| Iner-11/3.03/70.7 | (structure) |
| Iner-12/3.38/70.7 | (structure) |
| Iner-13/4.33/67.5 | (structure) |

TABLE 6-continued

| CODE/LogP/PSA | STRUCTURE |
|---|---|
| Iner-14/4.74/67.5 | (structure) |
| Iner-5/4.41/67.5 | (structure) |
| Iner-16/3.46/70.7 | (structure) |
| Iner-17/3.80/70.7 | (structure) |
| Iner-18/4.75/67.5 | (structure) |

TABLE 6-continued

| CODE/LogP/PSA | STRUCTURE |
|---|---|
| Iner-19/5.17/67.5 | 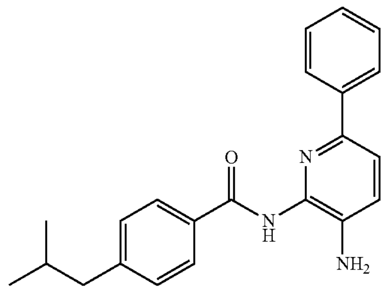 [SMILES: CN(C)Cc1ccc(C(=O)Nc2nc(-c3ccccc3)ccc2N)cc1] |
| Iner-20/4.84/67.5 | 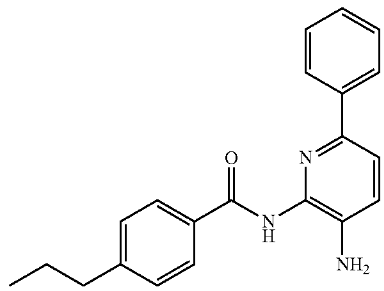 [SMILES: CCCc1ccc(C(=O)Nc2nc(-c3ccccc3)ccc2N)cc1] |

3) Benzene Ring C Substituted with Pyridine:

TABLE 7

| CODE/LogP/PSA | STRUCTURE |
|---|---|
| Iner-21/2.74/70.7 | 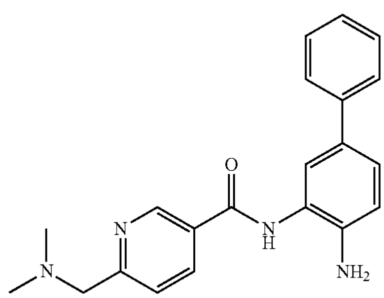 |
| Iner-22/3.38/70.7 | 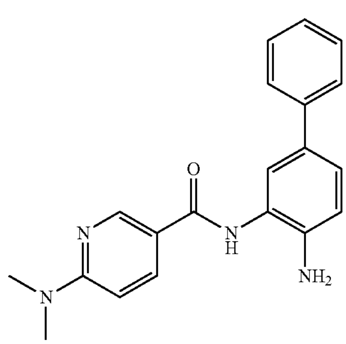 [SMILES: CN(C)c1ccc(C(=O)Nc2cc(-c3ccccc3)ccc2N)cn1] |

TABLE 7-continued

| CODE/LogP/PSA | STRUCTURE |
|---|---|
| Iner-23/3.96/67.5 | 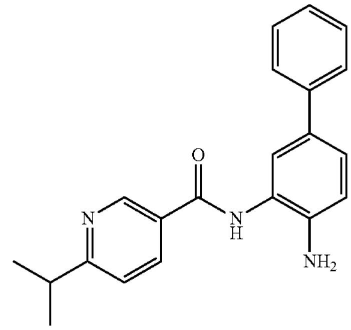 |
| Iner-24/4.31/67.5 | 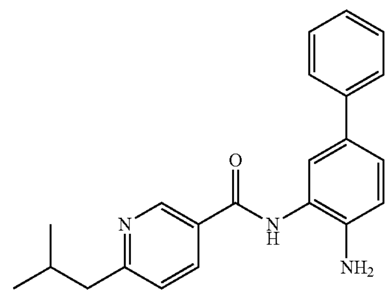 |
| Iner-25/3.98/67.5 | 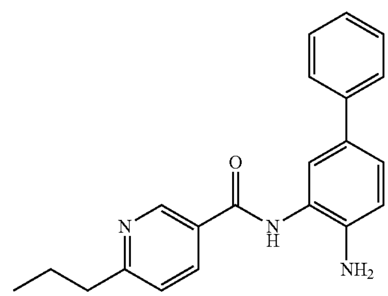 |
| Iner-26/2.74/70.7 | 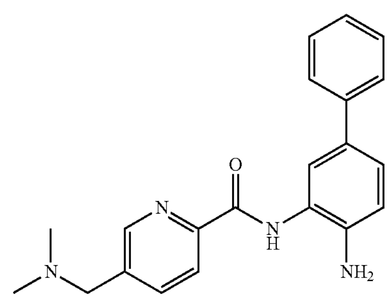 [SMILES: CN(C)Cc1ccc(C(=O)Nc2cc(-c3ccccc3)ccc2N)nc1] |
| Iner-27/3.08/70.7 | 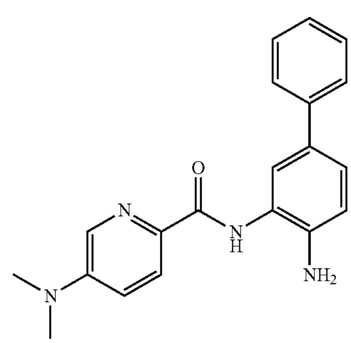 [SMILES: CN(C)c1ccc(C(=O)Nc2cc(-c3ccccc3)ccc2N)nc1] |

TABLE 7-continued

| CODE/LogP/PSA | STRUCTURE |
|---|---|
| Iner-28/4.03/67.5 | *[structure: 5-isopropyl-pyridine-2-carboxamide linked to 2-amino-5-phenyl-phenyl]* |
| Iner-29/4.45/67.5 | *[structure: 5-isobutyl-pyridine-2-carboxamide linked to 2-amino-5-phenyl-phenyl]* |
| Iner-30/4.12/67.5 | *[structure: 5-propyl-pyridine-2-carboxamide linked to 2-amino-5-phenyl-phenyl]* |

What is claimed is:

1. A compound is selected from the group consisting of a group 1, a group 2, and a group 3, wherein the group 1 consists of (1) BNL-26-F18, (2) BNL-26a-F18, (3) BNL-26b-F18, (4) BNL-26c-F18, and (5) BNL-26d-F18 as shown below:

(1)

*[structure of [$^{18}$F]N-(4-amino-4'-fluoro-[1,1'-biphenyl]-3-yl)-4-((dimethylamino)methyl)benzamide]*

[$^{18}$F]N-(4-amino-4'-fluoro-[1,1'-biphenyl]-3-yl)-4-((dimethylamino)methyl)benzamide, (2)

*[structure of [$^{18}$F]N-(4-amino-4'-fluoro-[1,1'-biphenyl]-3-yl)-4-(dimethylamino)benzamide]*

[$^{18}$F]N-(4-amino-4'-fluoro-[1,1'-biphenyl]-3-yl)-4-(dimethylamino)benzamide, (3)

*[structure of [$^{18}$F]N-(4-amino-4'-fluoro-[1,1'-biphenyl]-3-yl)-4-isopropylbenzamide]*

[$^{18}$F]N-(4-amino-4'-fluoro-[1,1'-biphenyl]-3-yl)-4-isopropylbenzamide, (4)

*[structure of [$^{18}$F]N-(4-amino-4'-fluoro-[1,1'-biphenyl]-3-yl)-4-isobutylbenzamide]*

[$^{18}$F]N-(4-amino-4'-fluoro-[1,1'-biphenyl]-3-yl)-4-isobutylbenzamide, and

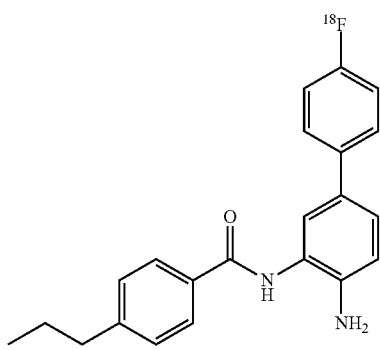

[$^{18}$F]N-(4-amino-4'-fluoro-[1,1'-biphenyl]-3-yl)-4-propylbenzamide;

the group 2 consists of (1) BNL-26-CCF18, (2) BNL-26a-CCF18, (3) BNL-26b-CCF18, and (4) BNL-26c-CCF18 as shown below:

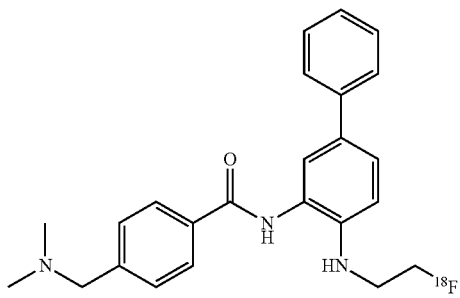

[$^{18}$F]4-((dimethylamino)methyl)-N-(4-((2-fluoroethyl)amino)-[1,1'-biphenyl]-3-yl)benzamide,

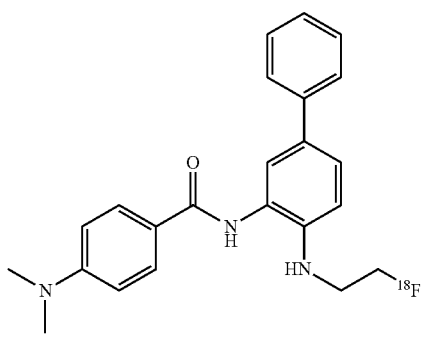

[$^{18}$F]4-(dimethylamino)-N-(4-((2-fluoroethyl)amino)-[1,1'-biphenyl]-3-yl)benzamide,

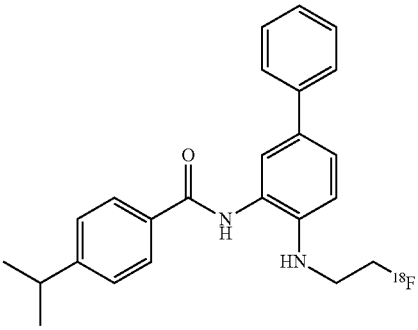

[$^{18}$F]N-(4-((2-fluoroethyl)amino)-[1,1'-biphenyl]-3-yl)-4-isopropylbenzamide, and

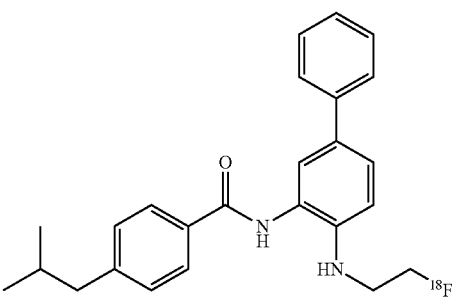

[$^{18}$F]N-(4-((2-fluoroethyl)amino)-[1,1'-biphenyl]-3-yl)-4-isobutylbenzamide; and the group 3 is (1) BNL-26-CBF 18 as shown below:

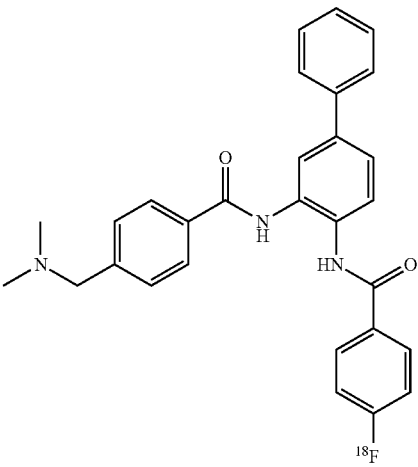

[$^{18}$F]4-((dimethylamino)methyl)-N-(4-(4-fluorobenzamido)-[1,1'-biphenyl]-3-yl) benzamide.

2. An imaging agent comprising a compound of claim 1 and an HDAC inhibitor.

3. A method of synthesizing the compound selected from the group consisting of the group 1, the group 2, and the group 3 of claim 1, wherein the method of synthesizing the compound of the group 1 in which the radionuclide $^{18}$F is labeled on the para-position of a benzene ring as shown below:

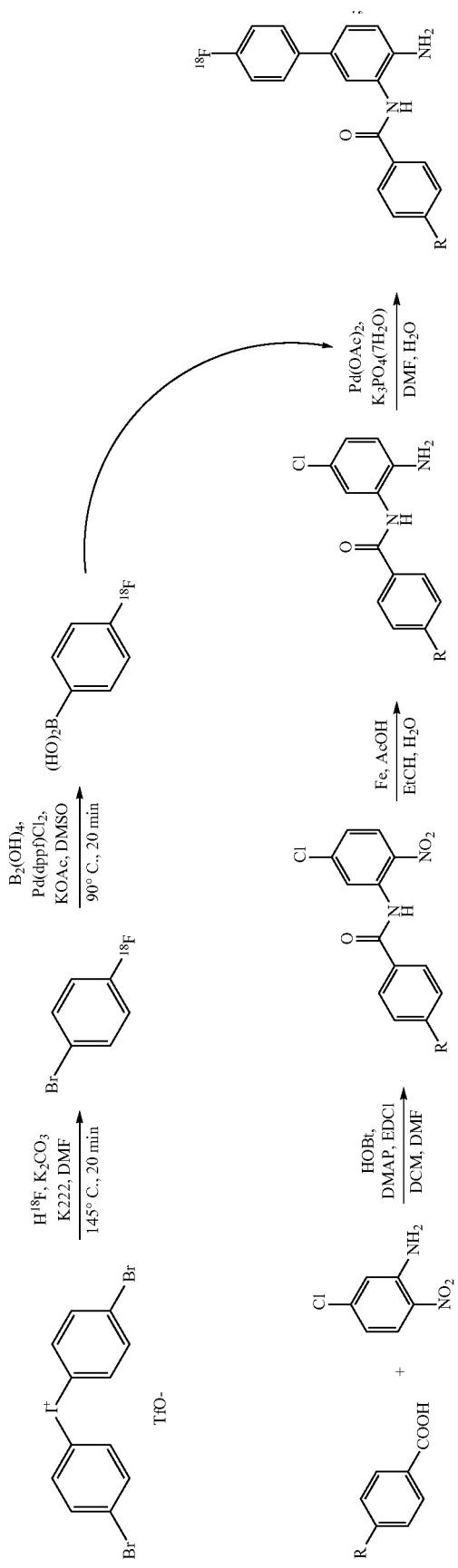

wherein the method of synthesizing the compound of the group 2 of claim 1 in which the radionuclide $^{18}$F is labeled on the NH$_2$ of a benzene ring, BNL-26-(CH$_2$)$_n$$^{18}$F, n=2 or 3, consisting of two types, as shown below:

(1) first type of labeling BNL-26-CH$_2$CH$_2$$^{18}$F placing di-p-toluene sulfonic acid terephthalate TsOCH$_2$CH$_2$OTs and $^{18}$[F]F$^-$K$^+$ APE 2.2.2 in methanol and heating to about 85° C. for about 5 minutes to form TsOCH$_2$CH$_2$$^{18}$F;

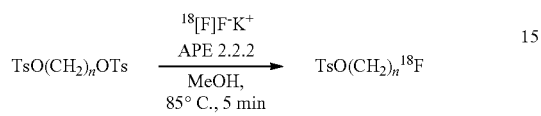

placing BNL-26 and labeled TsOCH$_2$CH$_2$$^{18}$F in methanol and heating to about 85° C. for about 5 minutes, forming BNL-26-CH$_2$CH$_2$$^{18}$F;

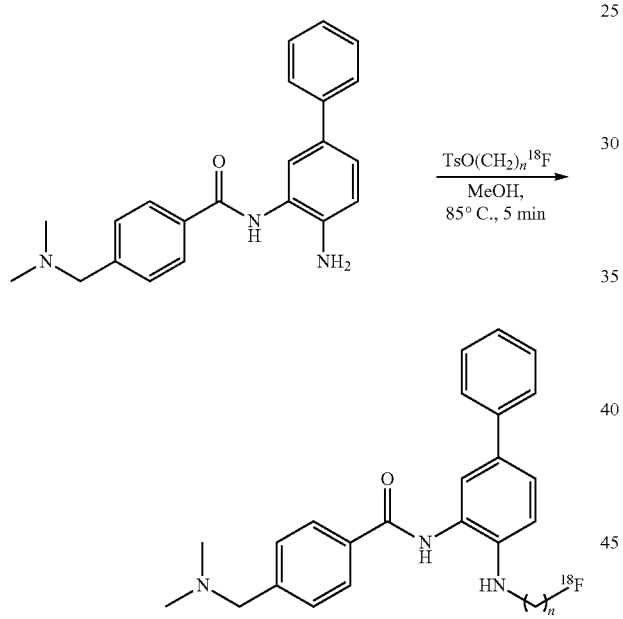

(2) Second type of labeling BNL-26-CH$_2$CH$_2$$^{18}$F placing TsOCH$_2$CH$_2$OTs and BNL-26 in methanol and heating to about 85° C. for about 5 minutes to form BNL-26-CH$_2$CH$_2$OTs;

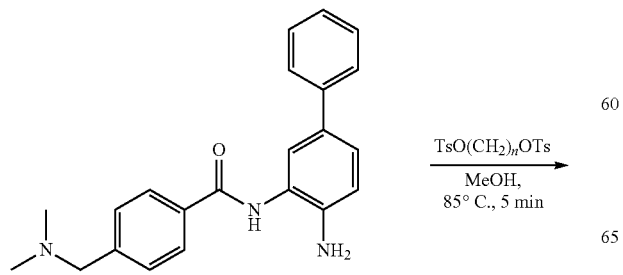

placing BNL-26-CH$_2$CH$_2$OTs and $^{18}$[F]F$^-$K$^+$ APE 2.2.2 in methanol and heating to about 85° C. for about 5 minutes,

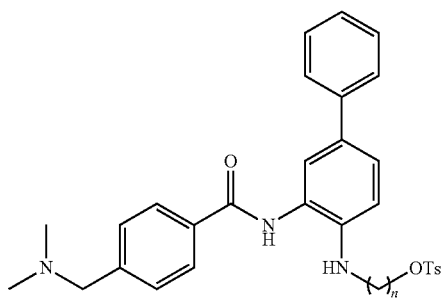

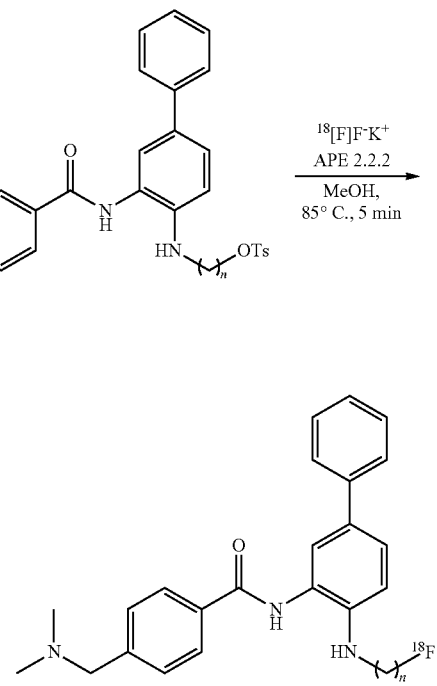

and forming BNL-26-CH$_2$CH$_2$$^{18}$F;

wherein the method of synthesizing the compound of the group 3 of claim 1 in which the radionuclide $^{18}$F is labeled on the NH$_2$ of a benzene ring through benzene amide structure as shown below:

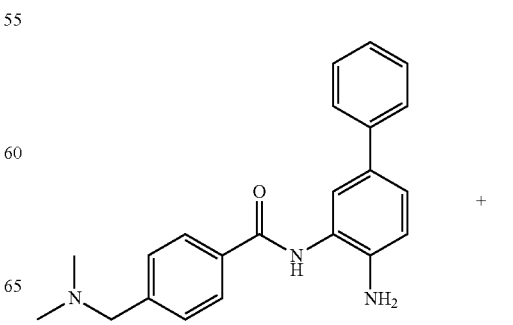

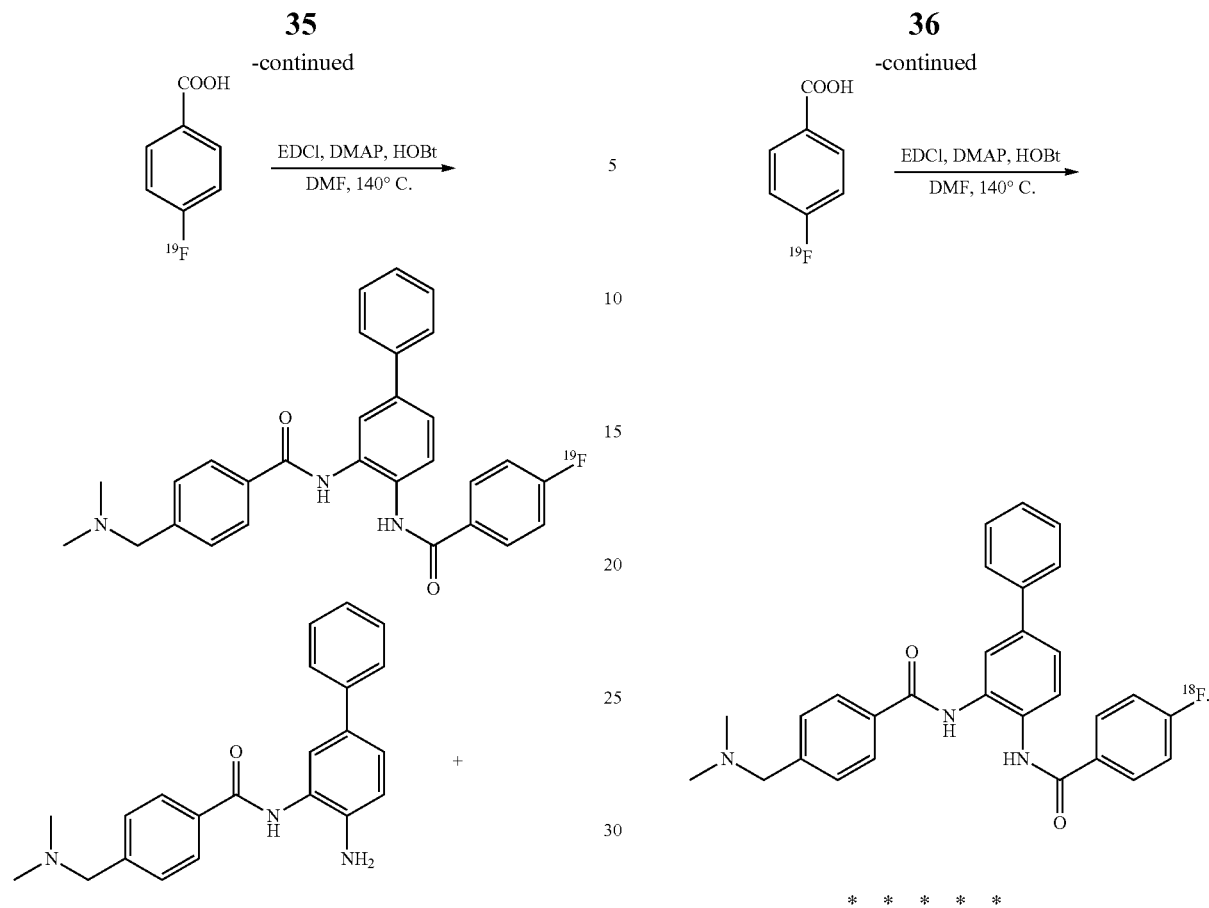
* * * * *